United States Patent
Lee et al.

(10) Patent No.: US 9,617,507 B2
(45) Date of Patent: Apr. 11, 2017

(54) APPARATUS AND METHOD FOR CULTURING CELLS AND TISSUE

(71) Applicant: IonOptix LLC, Milton, MA (US)

(72) Inventors: Peter G. W. Lee, Toronto (CA); Douglas L. Tillotson, Milton, MA (US); Richard T. Udale, Rosindale, MA (US); Katherine L. Barber, Randolph, MA (US)

(73) Assignee: IONOPTIX LLC, Westwood, MA (US)

( * ) Notice: Subject to any disclaimer, the term of this patent is extended or adjusted under 35 U.S.C. 154(b) by 366 days.

(21) Appl. No.: 14/042,871

(22) Filed: Oct. 1, 2013

(65) Prior Publication Data

US 2014/0113345 A1 Apr. 24, 2014

Related U.S. Application Data (60) Provisional application No. 61/717,987, filed on Oct. 24, 2012.

(51) Int. Cl.
*C12M 1/42* (2006.01)
(52) U.S. Cl.
CPC ............ *C12M 35/02* (2013.01); *C12M 35/04* (2013.01)
(58) Field of Classification Search
CPC ....... C12M 35/00; C12M 35/02; C12M 35/04
USPC ...................................... 435/285.2
See application file for complete search history.

(56) References Cited

U.S. PATENT DOCUMENTS

| | | | |
|---|---|---|---|
| 4,940,853 A * | 7/1990 | Vandenburgh | C12M 35/04 435/395 |
| 6,114,164 A * | 9/2000 | Dennis | C12M 35/02 435/287.1 |
| 7,148,059 B1 | 12/2006 | Tillotson et al. | |
| 2007/0178584 A1 | 8/2007 | Naruse et al. | |

FOREIGN PATENT DOCUMENTS

CN 1932511 * 7/2009
WO 2008123508 A1 10/2008

OTHER PUBLICATIONS

CN100514059 machine translation corresponding to CN1932511 (Jul. 2009).*

* cited by examiner

*Primary Examiner* — Gautam Prakash
(74) *Attorney, Agent, or Firm* — Michael W. Ferrell (57) ABSTRACT

An apparatus that provides synchronized chronic electrical stimulation and chronic stretch to a cell culture or tissue. The apparatus includes a programmable controller which synchronizes stretch and electrical stimulation applied to a deformable culture container, such as a silicone rubber culture dish. The apparatus is used to treat cells and retard de-differentiation or promote differentiation and maturation in some applications.

21 Claims, 8 Drawing Sheets

ARRHYTHMIA SEQUENCE

FIG. 10

EXERCISE PROTOCOL

APPARATUS AND METHOD FOR CULTURING CELLS AND TISSUE

CLAIM FOR PRIORITY

This non-provisional application claims the benefit of the filing date of U.S. Provisional Patent Application Ser. No. 61/717,987, of the same title, filed Oct. 24, 2012. The priority of U.S. Provisional Patent Application Ser. No. 61/717,987 is hereby claimed and the disclosure thereof is incorporated into this application by reference.

TECHNICAL FIELD

The present invention relates to an apparatus for culturing cells and tissue by synchronized application of electrical stimulation and physical stretch.

BACKGROUND

It is known that chronic electrical stimulation of cultured cardiac myocytes prevents atrophy and de-differentiation, maintaining contractile properties of the cells and tissue for much longer than unstimulated cells. One preferred system for providing electrical stimulation to cell cultures or "pacing" cell cultures as the process is known is disclosed in U.S. Pat. No. 7,148,059 to Tillotson et al. Among the features of the apparatus of the '059 patent are that it provides adjustable output voltage and current in order to work with standard culture dishes or flasks, and to work with different preparations. The system also serves as a stand alone programmable instrument that, once programmed, requires no monitoring. A further advantageous aspect of the system is that electrolysis by-products that naturally accumulate in a closed system during prolonged electrical stimulation are minimized. This latter feature is accomplished through the use of appropriate electrode material, alternating pulse polarity and by employing circuitry which prevents current leakage between pulses.

It is likewise known in the art that chronic mechanical stretch or physical stimulation has beneficial effects on cell and tissue cultures, promoting cell vitality and reducing tendencies of the cultured cells to de-differentiate. One culture device for applying uniform stretch to cells is disclosed in United States Patent Application Publication No. US 2007/0178584 of Naruse et al., wherein a deformable culture well is provided. See, also, WO 2008/123508 wherein a fertilized egg is physically stimulated by deforming a channel in which the egg is incubated.

Despite advances in the art, existing systems are relatively limited in providing culture stimulation options for cellular research and product development.

SUMMARY OF INVENTION

There is provided in accordance with the invention, an apparatus and method for providing electrical stimulation or pacing to cultured cells and tissue which is synchronized to stretch events applied to the culture. In this way, novel mechanical/electrical stimulation regimens are provided to cells and tissue, allowing for more options to stimulate the cells in a more physiologically-relevant manner than heretofore possible. The inventive method and apparatus thus provides novel means to delay de-differentiation and cell atrophy of a culture under study by application of both electrical stimulation/stretch in a controlled manner. Likewise, the complex electrical/stretch stimulus applied may be used to promote differentiation of undifferentiated cells such as stem cells to cardiac cells, for example, and promote maturation of differentiated stem cells, making possible the replacement of diseased tissue. Furthermore, the inventive apparatus can be used to study trauma/recovery of neurons, neurolemmocytes or other tissue by inflicting controlled trauma to cells followed by electrical stimulation and stretch.

Figure 1:
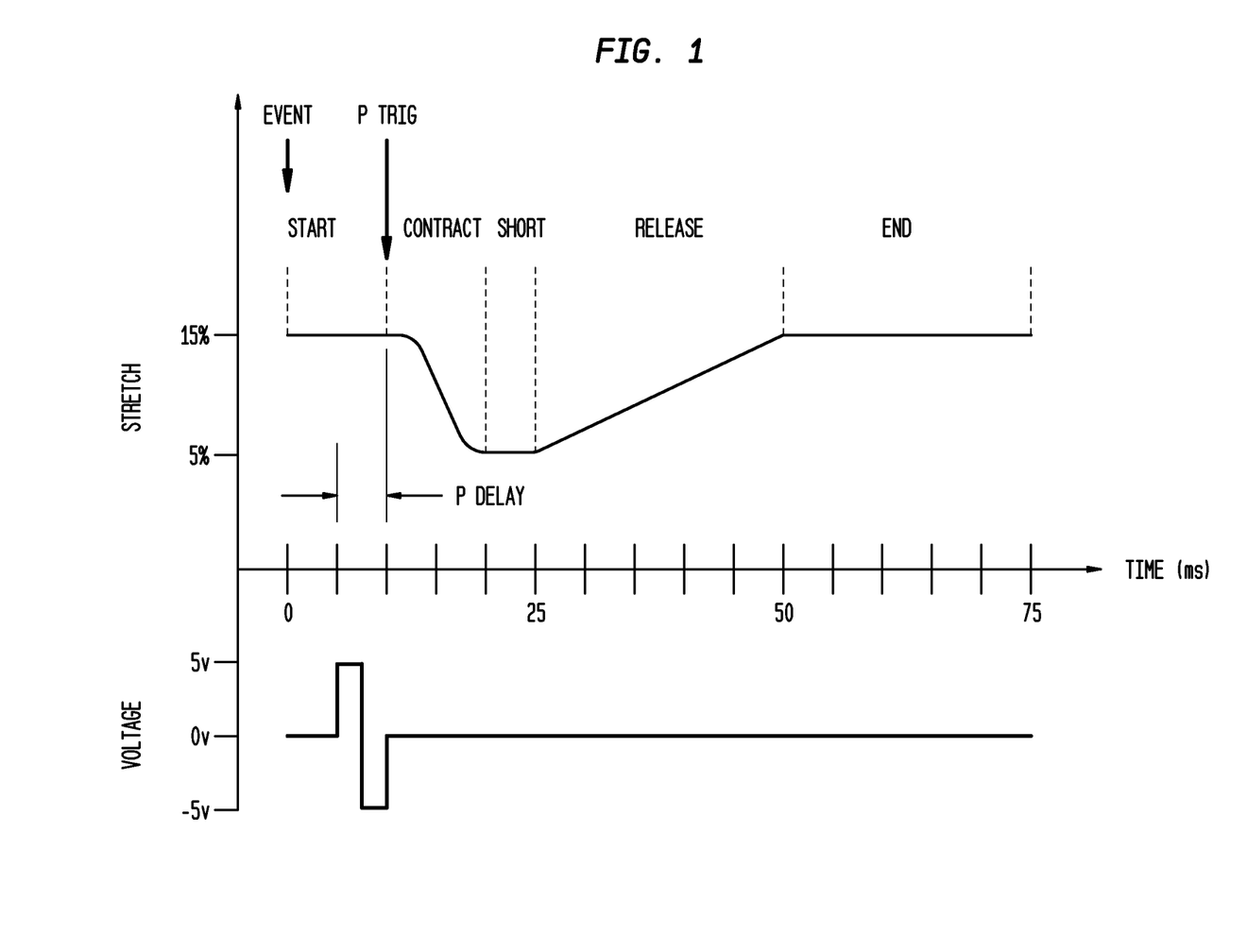
FIG. 1 is a graphical representation of synchronized electrical stimulation and stretch applied to cells in accordance with the invention.

The invention is appreciated by reference to FIG. 1, which is a graphical representation of synchronized electrical stimulation and stretch applied to cultured cells over a 75 millisecond (ms) time interval.

In FIG. 1, there is shown at the upper portion a stretch regiment applied to a cell culture; the regimen having five (5) parts: (a) a start phase of 10 ms with 15% stretch applied to the culture; (b) a contract phase of 10 ms wherein the stretch is reduced to 5%; (c) a short phase where the contracted length is maintained at 5% stretch for 5 ms; (d) a release phase where the cell culture is stretched to 15% over 25 ms; and (e) an end phase for the remainder of the 75 ms event where the culture is maintained at 15% stretch.

In the lower portion of FIG. 1, there is shown electrical stimulation applied to the cell culture during the same 75 ms interval as the applied stretch described above and shown in the upper part of FIG. 1. A pulse stimulation is pre-programmed to "trigger" 5 ms before the start of the "contract" phase and apply a bimodal +/−5 volt pulse to the cultured cells over a 5 ms interval between 5-10 ms of the 75 ms cell treatment illustrated. In FIG. 1, Event represents the beginning of the synchronized electrical stimulation/stretch cycle, P Trig represents the pulse trigger for electrical stimulation and P Delay indicates a −5 ms trigger delay for electrical stimulation.

The combined electrical/stretch stimuli shown in FIG. 1 may be immediately repeated or sequenced with another treatment including electrical stimulation, stretch, both, or neither stretch nor electrical stimulation as will be appreciated from the discussion which follows.

Specific embodiments and illustration of construction and operation of the inventive system and method as well as further aspects and advantages of the present invention will become apparent from the detailed discussion which follows.

DESCRIPTION OF DRAWINGS

The invention is described in detail below in connection with numerous examples and in connection with the attached Figures wherein like numerals designate like parts. In the Figures.

DETAILED DESCRIPTION

The invention is described in detail below in connection with the Figures for purposes of illustration, only. The invention is defined in the appended claims. Terminology used throughout the specification and claims herein are given their ordinary meanings as supplemented by the discussion immediately below, for example, ms refers to milliseconds, Hz refers to frequency in cycles per second, V refers to electrical potential in volts and so forth.

"Chronic" as used herein refers to the recurring application of electrical stimulation and the recurring application of stretch to a specimen.

Since the inventive system can impart electrical pulses and mechanical stretch onto the cells (in combination or singly), the term pacing frequency or stimulation frequency becomes somewhat confusing as they are both electrical-pulse-based terminology. "Event" is a neutral term divorced from electrical or stretch inspired terminology. As used herein an "Event" is an internally generated signal that triggers the physical electrical pulse or mechanical stretch or the repeat frequency of a synchronized electrical stimulation/stretch combined cycle. When a frequency is programmed via one of the LCD menus of the controller, one is programming the Event frequency. It is these Events that subsequently trigger (possibly with a delay) the desired electrical pulse or stretch.

"Myocytes" refers to contractile biological cells, such as skeletal and cardiac muscle cells.

"Stretch" refers to physical deformation applied to a specimen disposed in a deformable culture container by virtue of deformation of a wall of the container. "% stretch" refers to linear elongation from a fully contracted state, that is, no stretch (strain) at all applied to a culture dish. 0% stretch corresponds to a fully contracted specimen, whereas 5% or so stretch is typical for a "short" phase to simulate systolic cardiac contraction of a myocyte. A higher value of stretch indicates an elongated state. 15% or so stretch may be used to simulate diastolic action, for example.

Figure 8:
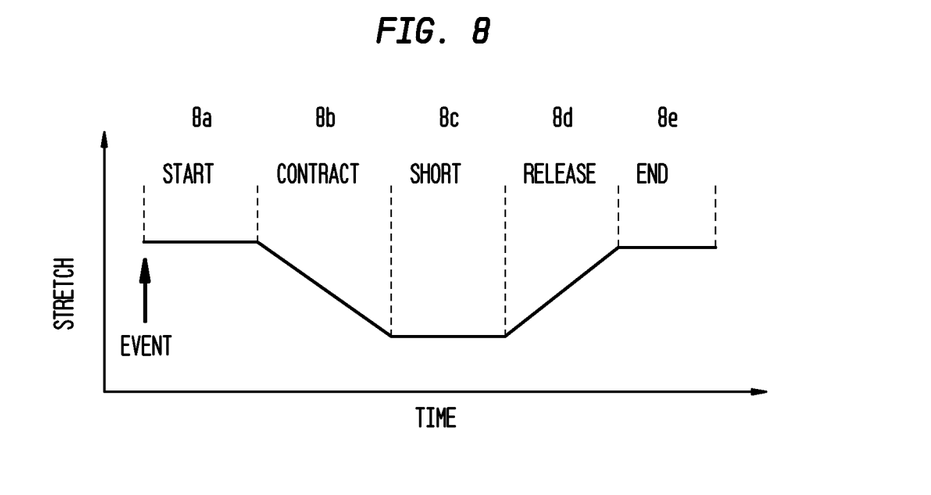
FIG. 8 is a graphical illustration of a stretch cycle used in accordance with the invention to provide mechanical stimulation to cells.

"Stretch pre-load" refers to the amount of stretch at the beginning and end of a stretch operation as shown in FIGS. 1 and 8 and discussed hereinafter.

"Synchronized" and like terminology as used herein refers to temporal coordination, for example, of electrical stimulation and stretch applied to a test specimen such that there is a predetermined temporal relationship between the electrical stimulation and stretch. In a typical embodiment, an Event is used as a reference and electrical stimulation or stretch is applied at a fixed interval or simultaneously with the Event.

Figure 2:
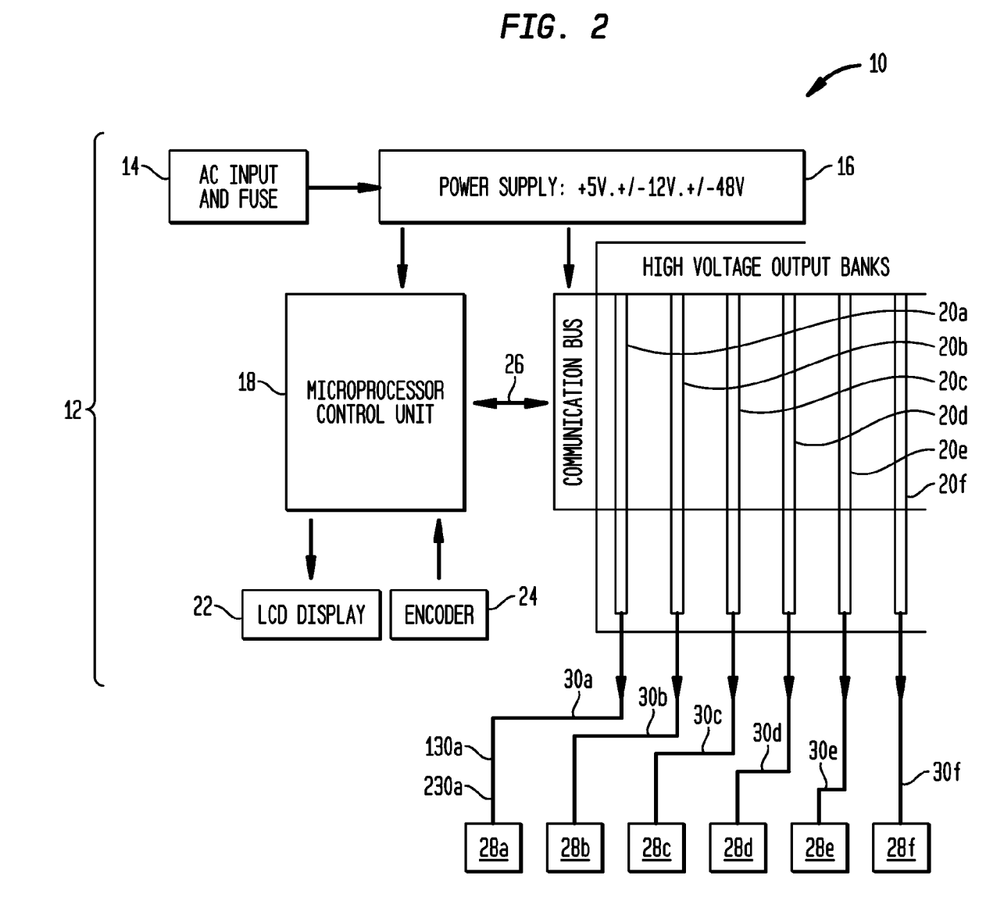
FIG. 2 is a block diagram of the apparatus of the present invention.

Referring to FIG. 2, the inventive apparatus 10 is shown schematically in a block diagram. A programmable controller 12 includes an AC input and fuse unit 14 which feeds a power supply 16 which provides power to microprocessor control unit 18 and a plurality of high voltage output banks indicated at 20a, 20b, 20c, 20d, 20e, and 20f. The microprocessor control unit is coupled to an LCD display 22 and an encoder 24 for purposes of programming the device.

Control unit 18 communicates with output banks 20a-f via a communications bus 26 and thus controls banks 20a-20f which supply electrical stimulation and stretch signals to a plurality of electromechanical stages indicated at 28a, 28b, 28c, 28d, 28e, 28f, each of which includes culture containers, supports for stretching the containers and electrodes. Each of the output banks also includes a microprocessor (not shown) for purposes of controlling output signals to the electromechanical stage and specimen via a plurality of outputs indicated generally at 30a, 30b, 30c, 30d, 30e, and 30f. The output banks supply electrical stimulation or pacing to specimens as generally described in U.S. Pat. No. 7,148,059, the disclosure of which is incorporated herein by reference and further discussed below. The pacing features of apparatus 10 are generally conventional and are resident in the C-Pace EP culture pacer available from IonOptix LLC of Milton, Mass. The electrical stimulation only output banks generally have the following properties:

Frequency: 0.010-99 Hz;
Pulse duration: 0.4-24 ms;
Voltage: +/−40V and 240 mA;
Bipolar stimulation pulses;
Short circuit and open circuit protection;
Digital inputs and outputs;
Programmable multi-step protocols.

Output banks, which support both electrical stimulation and stretch, are constructed on a circuit board compatible with the C-Pace EP chassis, have similar characteristics and include the following components:

| Description | Manufacturer |
|---|---|
| P8X32A Multi-core microcontroller | Parallax Inc/ Rocklin, California |
| R325 Stepper Driver | Lin Engineering/ Morgan Hill, California |
| N- & P-Channel MOSFETs (ex. FQP50N06L, FQP47P06) Push-pull amplifier (for electrical stimulator) | Fairchild Semiconductor/ San Jose, California |
| LTC7541 Digital-to-analog converter (for electrical stimulator) | Linear Technology/ Milpitas, California |
| ADG408 Analog multiplexer (for electrical stimulator) | Analog Devices/ Norwood, Massachusetts |

Output banks, which support both stretch and electrical stimulation generally, have the following characteristics:
Event Parameters
  Frequency: 0.010 to 10 Hz
Stretch Parameters
  stretch and release waveforms;
  systolic and diastolic dwell times (limits defined by event frequency);
  from 0%-30% stretch;
  from 0%-30% stretch pre-load;
  stretch cycles are triggered by Events on a programmable basis relative to electrical stimulations (1:1, 1:2, etc described hereinafter).
Electrical Stimulation Parameters
  pulse duration: 0.4-24 ms;
  voltage: up to +1-40;

trigger with variable delay from any stretch phase;
stimulation pulses triggered on a programmable basis relative to stretch cycles (1:1, 1:2, etc)

Electrical stimulation and/or stretch is applied to a specimen on a electromechanical stage 28a wherein a culture container is secured and electrodes are placed in the cavity of the culture container. Electromechanical stages 28b-28f may be the same or different, and may be used to apply both stretch and electrical stimulation, or electrical stimulation only or stretch only as will be appreciated from the discussion which follows. The various components are illustrated in FIGS. 3, 4, 5 and 6 and discussed in more detail below.

Figure 3:
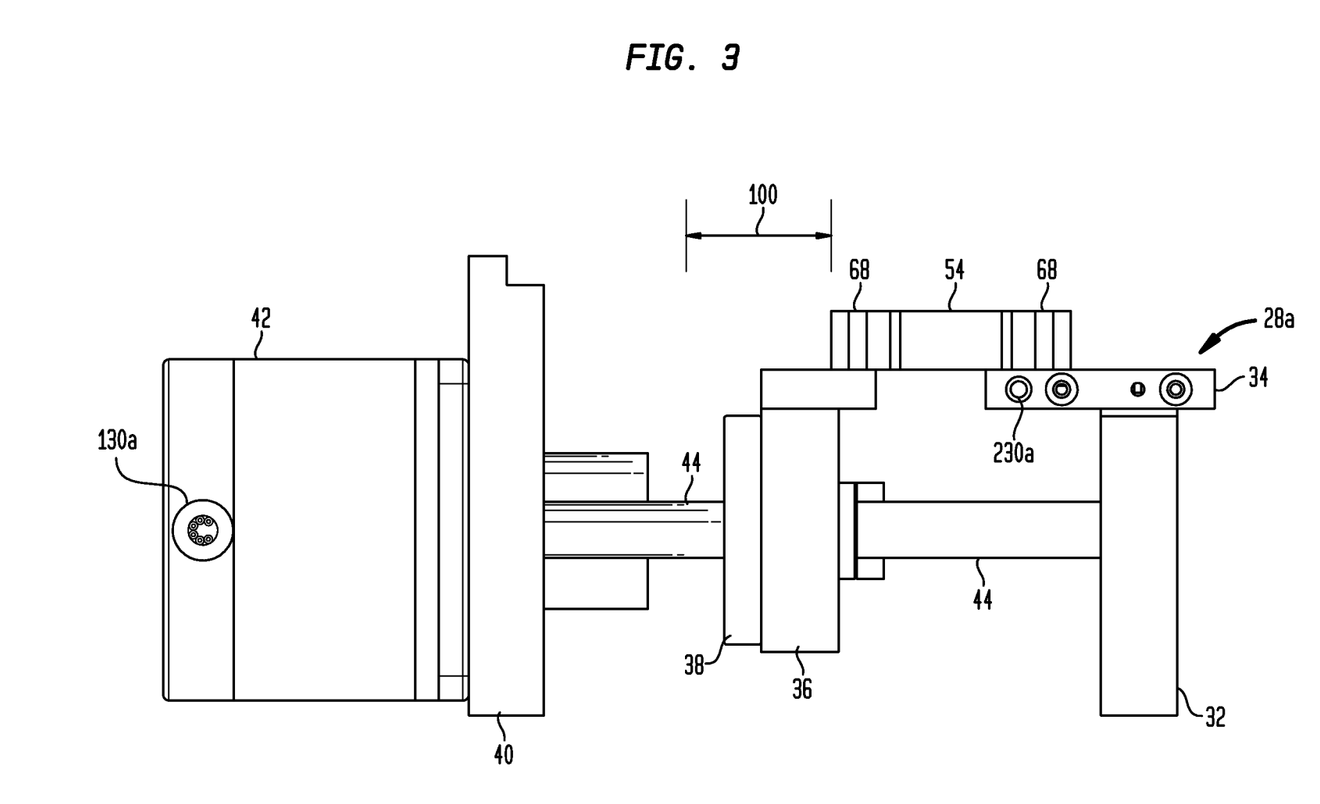
FIG. 3 is a side view of the electromechanical stage utilized as part of the inventive apparatus external to the controller wherein the electrode assembly has been removed.
Figure 4:
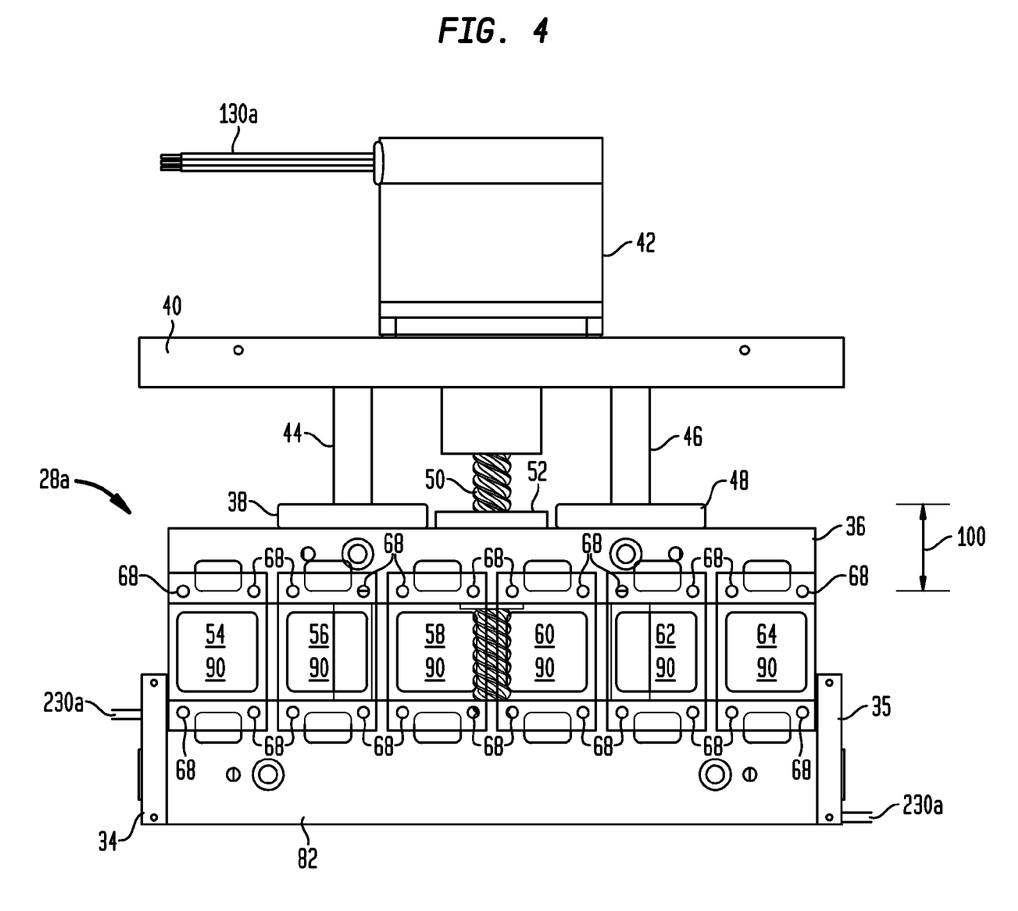
FIG. 4 is a top view of the electromechanical stage wherein the electrode assembly has been removed.

FIG. 3 is a side view of electromechanical stage 28a, wherein there is seen a fixed support 32, a stimulator contact 34 thereon, a moving support 36, a linear bearing 38, a motor mounting plate 40 and stepper motor 42. Additional components are also seen in FIG. 4, which is a top view of electromechanical stage 28a and motor 42, wherein like parts are designated by like numerals. There is shown another stimulator contact 35, a pair of guide rods 44, 46 and an additional linear bearing 48 as well as a drive screw 50 and a nut 52.

A plurality of culture dishes, six rectangular dishes in this case, culture dishes 54, 56, 58, 60, 62 and 64 are mounted to fixed support 32 and are mounted to movable support 36 by a plurality of mounting posts indicated by numeral 68.

The culture dishes are suitably made from silicone rubber or other heat resistant elastomer so that they can be sterilized if so desired. The motor is coupled to a stretch output 130a of an output 30a of a high voltage output bank 20a of programmable controller 12. To this end, output bank 20a of the controller has one or more stretch outputs for means of providing stretch using a stepper motor 42, for example. Alternatively, a stretch output such as 130a could drive one or more solenoids to provide a range of motion for moving support 36, if so desired.

The electrical stimulator contacts are powered by output 230a of an output 30a of bank 20a of controller 12 in synchronization with the stretch output as described hereinafter. Different polarities are provided to electrical contacts 34, as is appreciated from the various Figures.

Figure 5:
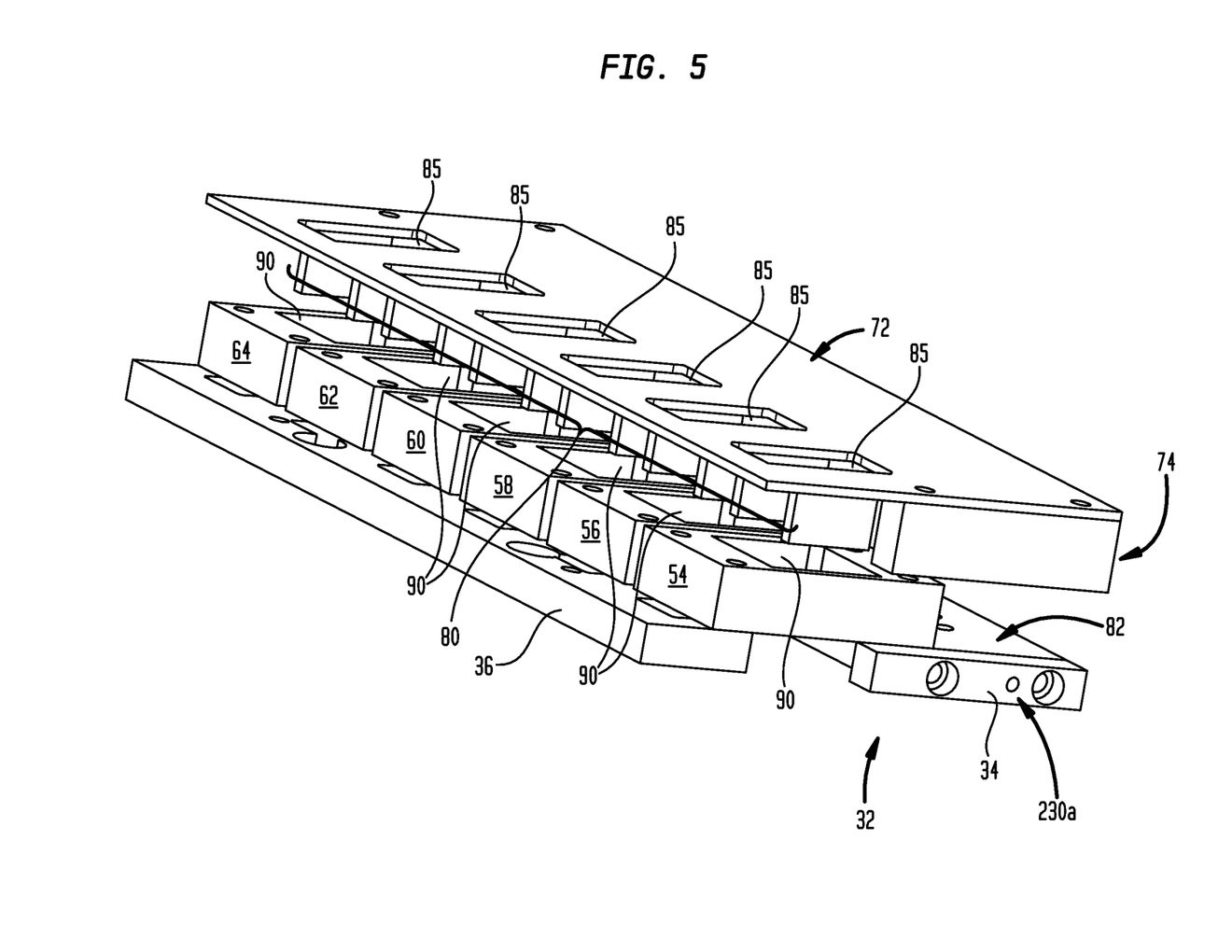
FIG. 5 is a view in perspective of a portion of the electromechanical stage external to the controller used to apply synchronized stretch and electrical stimulation to cell cultures.
Figure 6:
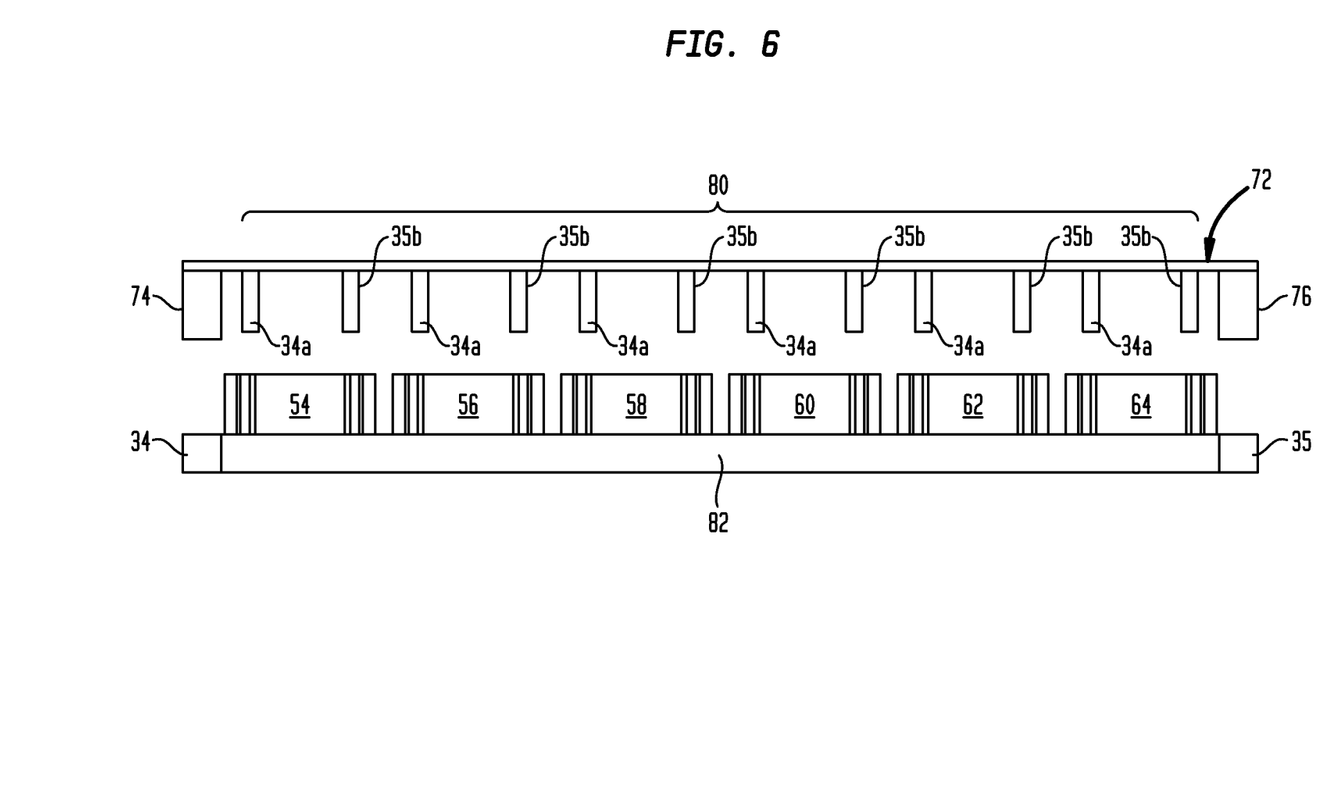
FIG. 6 is a back view of a portion of the electromechanical stage of the invention illustrating the relative positioning of electrodes used to stimulate cells in accordance with the invention.

Further components and assembly of the inventive apparatus are illustrated in FIGS. 5 and 6, which are partially exploded perspective and back views, respectively, illustrating assembly of the electrodes, culture dishes and supporting parts of the electromechanical stage upon which they are mounted. FIG. 5 shows culture dishes 54, 56, 58, 60, 62 and 64 mounted to fixed support 32 and moving support 36. A plurality of carbon electrodes are affixed to a printed circuit board 72 which, in turn, is mounted to engage stimulator contacts 34, 35 powered by output bank 20a by way of an electrical stimulation output 230a. To this end, board 72 has a corresponding pair of stimulator contacts 74, 76 which are placed in contact with stimulator contacts 34, 35 which then provides electrical pulses to the electrodes which are numbered as electrodes 80 in FIG. 5 and are indicated as electrode sets 34a, 35b in FIG. 6. That is, the board provides pulses through appropriate circuitry associated with the six pairs of electrodes from output 230a which preferably includes bipolar capability. Twelve (12) electrodes are provided for the six (6) culture dishes and are oriented orthogonally to the direction of stretch so they do not interfere with the motion of the dishes as they are stretched between various states of elongation. A pair of electrodes is supplied to each culture cavity or well as shown, one electrode communicating with contacts 34, 74 and one electrode communicating with contacts 35, 76. In FIG. 6, the electrodes of each set communicating with contacts 34, 74 are labeled 34a and the electrode of each set communicating with contacts 35, 76 is labeled 35b.

The fixed support is provided with an insulator 82 so that electrical pulses are not inadvertently applied to the culture dishes and to isolate polarity of the electrical stimulation.

So that a microscope may be used to observe cell cultures in the dishes, a plurality of viewing ports indicated at 85 are provided in the printed circuit board 72 which is mounted atop the culture dishes in the position indicated in FIGS. 5 and 6 such that the viewing ports are aligned with the dish wells and the culture is readily observable. These ports also allow culture medium to be renewed and changed.

To utilize the device, a cell or tissue specimen is prepared and adhered to culture containers such as culture dishes 54-64, optionally with an attachment factor such as a polylysine/fibronectin coating on the culture dish so that when the culture dish is stretched the cells are subjected to essentially the same stretch. The culture dish may have any suitable surface treatment or may adhere sufficiently to the cells without any surface treatment or attachment factor depending upon the required effect and the degree to which the cells and culture dish naturally adhere to one another. Other than a polylysine/fibronectin coating, one might apply, for example, a collagen based attachment factor or a MYO-TAK® biocompatible adhesive if needed. A suitable electrolytic medium is also provided. The electrolytic medium may be culture medium such as the commonly used Hanks' balanced solution; generally a medium which includes a salt and an amino acid is suitable. Alternatively, any medium which will conduct the electrical pulses may be used if so desired. The cells or tissue may be any cells or tissue of interest, such as cells selected from: myocytes; stem cells; induced pluripotent stem cell derived cells; neurons; and neurolemmocytes or immortalized cell lines derived from cells with a cardiac, smooth or skeletal muscle origin.

The culture dishes containing the specimens are mounted on an electromechanical stage such as stage 28a, affixed to fixed support 32 and movable support 36 as shown in FIGS. 3 and 4. After the culture dishes are mounted, circuit board 72 is placed atop the fixed support and secured thereto such that contacts 34, 74 and contacts 35, 76 are engaged and the electrode pairs 34a, 35b are submersed in the electrolytic medium of wells 90 of the culture dishes.

Programmable controller 12 is activated and provides chronic electrical stimulation to the electrodes 80 and a chronic stretch output to stepper motor 42 such that the electrical stimulation is synchronized to the stretch provided to the elastic culture dishes as they are stretched. The programmable controller may be activated in any number of ways, preferably with software providing operating options.

Figure 7:
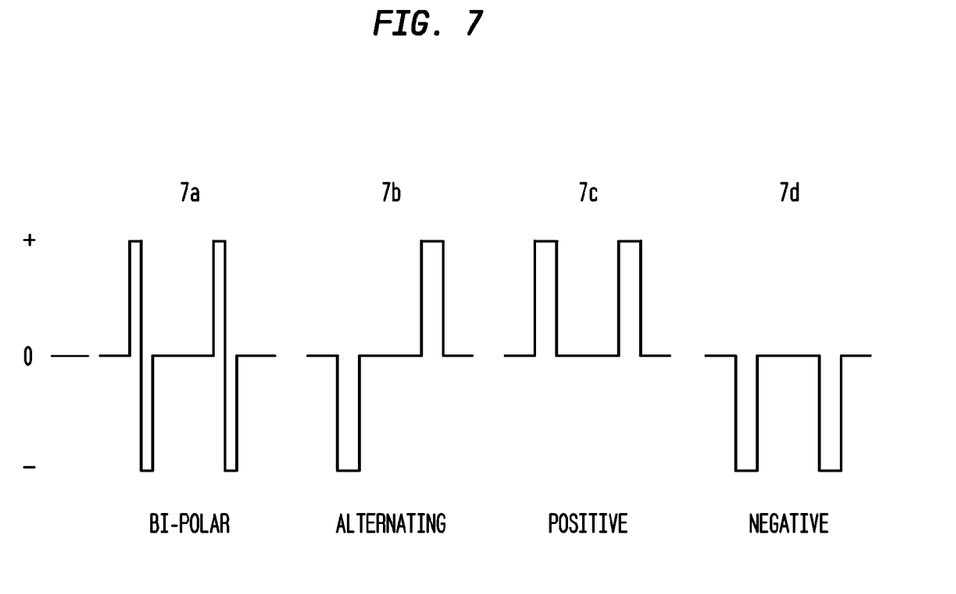
FIG. 7 is a schematic diagram illustrating bipolar electrical pulses and other pulses used in connection with the present invention.

Controller output 230a provides chronic electrical pulses to the contacts and the electrodes may be of numerous selected patterns, such as those shown schematically in FIG. 7. The chronic pulses can be bipolar, as shown at 7a, alternating as shown at 7b, positive as shown at 7c or negative as shown at 7d. These signals are synchronized to the stretch control output 130a provided by controller 12 to stepper motor 42. That is, control output 130a provides the stretch protocol to stepper motor 42 which controls rotation of drive screw 50 which is engaged to movable support 36 by way of nut 52 as is seen in FIG. 4. The position of movable support 36 is thus controlled over a range of motion 100 which imparts linear stretch from 0 to 30% to the culture dishes in the direction indicated at 100 by controlling the rotation of screw 50.

The stretch protocol applied to the sample is controlled by menu-driven software as discussed hereinafter and has the general features shown in FIG. 8. At the onset or the beginning "event" a stretch pre-load is maintained for a start phase, for example, at 20% linear elongation over a time interval indicated at 8*a*. The next phase of the stretch operation is a "contract" phase wherein movable support 36 is driven toward fixed support 32 by screw 50 and the culture dishes are shortened, for example, to 5% elongation as indicated at 8*b*. The dish remains shortened after a systolic dwell time of several milliseconds as indicated at 8*c* when the screw is motionless.

Thereafter, the screw rotation is reversed in a release phase wherein the sample dish is lengthened again to its initial pre-load length at the start of the operation. The release phase is illustrated schematically at 8*d* in FIG. 8. After the release phase, an end phase pause occurs as shown at 8*e*. The stretch operation may be repeated as so desired, up to repeat frequencies of 10-15 Hz depending upon equipment and power limitations and the amount of stretch (% stretch) involved in a particular operation.

Figure 9:
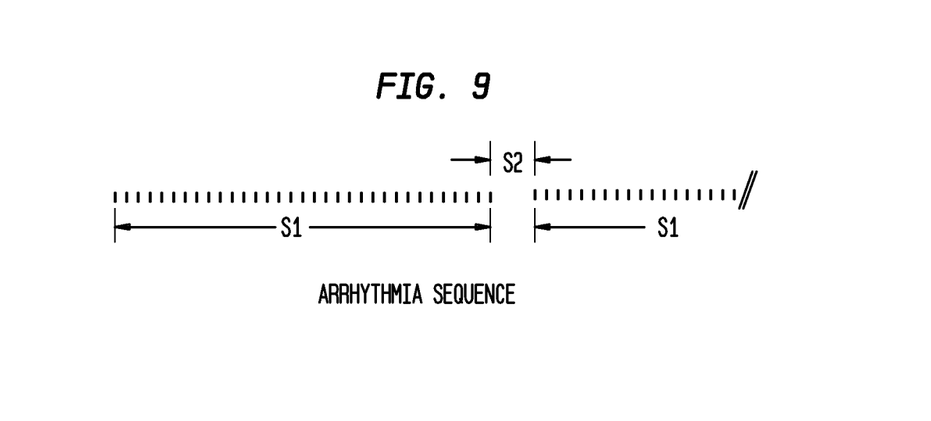
FIG. 9 is an illustration of electrical stimulation with pulse trains which mimic arrhythmia.
Figure 10:
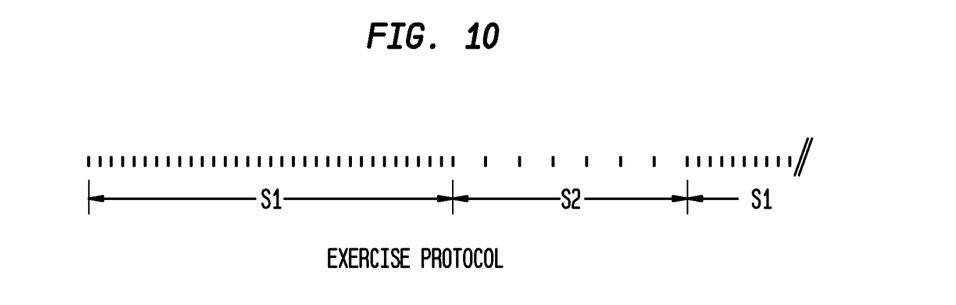
FIG. 10 is an illustration of electrical stimulation which mimics exercise.

A stretch operation may be synchronized with a variety of electrical stimulation or "pacing" protocols. There is shown in FIG. 9, for example, a pacing regimen which mimics arrhythmia. This protocol is programmed in controller 12 by defining a first step of a sequence to provide pulses with the desired frequency and length followed by a second step of a sequence defined to be a pulse train of the desired frequency with a duration of one pulse. Step 3 of the sequence is the end of the pacing sequence. FIG. 10 shows an exercise pacing protocol with individual frequency and duration. Step 1 of the sequence is defined as a pulse train with the desired frequency and length. Step 2 of the sequence is defined as another pulse train with a different, slower frequency and a defined length and step 3 is defined as the end of sequence.

In FIGS. 9 and 10, the sequences repeat until cancelled. That is, for Basic and Sequence Modes, the selected event pulse train continues so long as the bank is enabled.

In a typical embodiment, controller 12 provides a common set of menu options that permit configuring the stretch aspects of an output bank. These options are tightly integrated with the mode specific options. Preferred menu options include defining stretch cycles with 5 phases in total: three static phases and two dynamic phases as shown on FIGS. 1 and 8 and discussed earlier. The static phases are the start, short and end phases. The first dynamic phase is the contract phase, which moves from start to short while the second is the release phase, which moves from short to end. The actual amounts of stretch that correspond to the start and end phases are always identical in a preferred mode of operating the device. The cycle shown in FIG. 8 goes on and on. The pacer Event triggers this cycle. We begin immediately the start phase and then proceed on to the contract, short, release and, finally, end phases. The end phase always ends coincidentally with the end of the event window. The Tables below show some available programming options in the menu driven controller software of the inventive apparatus.

TABLE 1

| | Stretch options |
|---|---|
| Resting: 15% | Line 1: Start and End Stretch Amount (Preload) |
| Short: 05% | Line 2: Total Amount of Contraction |

TABLE 1-continued

| | Stretch options |
|---|---|
| Start: 05 ms | Line 3: Start phase duration, absolute/relative selection |
| Contract: 10 ms | Line 4: Contract phase duration |
| Short: 04 ms | Line 5: Short phase duration |
| Release: 10 ms | Line 6: Release phase duration |
| C Shape: Ramp | Line 7: Contract phase waveform |
| R Shape: Ramp | Line 8: Release phase waveform |
| P Trig: Cont | Line 9: Stim Pulse Trigger Option |
| P Delay: −15 ms | Line 10: Stim Pulse Delay |
| P Ratio: 01:01 | Line 11: Stim: Stretch Ratio |

Above is the stretch menu. There are 11 options which fall into 4 broad groups: the stretch amounts, the stretch timings, the stretch shapes and the pacing options.

TABLE 2

| Stretch Amounts |
|---|
| Resting: 15% |
| Short: 05% |
| Start: 05 ms |
| Contract: 10 ms |

The resting and short lengths of the tissue are set via the first two menu lines. The resting length corresponds to the amount of stretch in the start and end phases of a stretch cycle while the short length corresponds to the amount of stretch in the short phase.

These values are both specified as a percent stretch, where 0% indicates no stretch. It may be a bit counterintuitive that the resting value is larger than the short value so keep in mind that no stretch is the shortest length the tissue can be. This would correspond to the maximum contraction in the case of myocytes. The percent contraction is calculated via the following equation:

percent contraction=(resting—short)/(resting)*100

TABLE 3

| Stretch Phase Durations |
|---|
| Start: 05 ms |
| Contract: 10 ms |
| Short: 04 ms |
| Release: 10 ms |

There are 4 stretch phase durations. It is unnecessary to specify the duration for the end phase as its duration is simply whatever amount of time is left over in the Event Window.

These timings can be set as absolute millisecond values or as a percentage of the event window in which the stretch is running. One selects between absolute or relative in the Start line. There, one clicks the Encoder after setting the value, and is able to select either ms or %. This setting applies to all stretch timings including the Pulse Delay and all timing related menu lines will display the ms or % units as appropriate.

The duration of any static phase (start, short or end) can be set to zero. The dynamic phases will have minimum durations that are determined by the waveform shape and the stretch amounts.

If the timings are relative, the sum of the 4 phases cannot be greater than 100.

TABLE 4

Phase Waveforms

| | |
|---|---|
| ^ | Release: 10 ms |
| — | C Shape: Ramp |
|   | R Shape: Ramp |
| ^ | P Trig: Cont |

The shape of the stretch for the Contract and Release phases can be specified individually from the available waveforms.

Ramp A ramp is simply a straight line from the start stretch amount to the end stretch amount.

Sine The sine transition uses one half of a sine wave, starting as appropriate at either the peak or the trough. If one uses a sine for both the Contract and Release phases with a zero duration Short phase, there is a full sine profile.

TABLE 5

Pulse Trigger and Delay

| | |
|---|---|
| ^ | R Shape: Ramp |
| — | P Trig: Cont |
|   | P Delay: −15 ms |
|   | P Ratio: 01:01 |

The Pulse Trigger (P Trig) and Pulse Delay (P Delay) settings together determine when the electrical stimulus pulse will be presented relative to the stretch waveform. The Pulse Trigger is always the beginning of a phase. Thus the selections for the trigger are simply the five phases as illustrated in the table below.

TABLE 6

Pulse Trigger Settings

| P Trig Setting | Trigger Phase |
|---|---|
| Star | Start |
| Cont | Contract |
| Shor | Short |
| Rel | Release |
| End | End |

Once the trigger is selected the Pulse Delay is applied to arrive at the exact moment the stimulus pulse will start. The delay can be positive or negative. A positive value puts the pulse after the trigger while a negative value will put it before the trigger. The values are bounded such that the pulse will never precede the start phase or follow the end phase. The units for the delay are the same as those selected for the Stretch Phase Durations: ms or %.

FIG. 1 illustrates a complete stretch-stimulation waveform, using the programming data provided in Tables 7 and 8 below.

TABLE 7

Synchronized Operation Parameters

Stretch Parameters

| | |
|---|---|
| Resting: | 15% |
| Short: | 05% |
| Start: | 02 ms |
| Contract: | 02 ms |
| Short: | 01 ms |
| Release: | 05 ms |

TABLE 7-continued

Synchronized Operation Parameters

| | |
|---|---|
| C Shape: | Sine |
| R Shape: | Ramp |
| P Trig: | Cont |
| P Delay: | −01 ms |
| P Ratio: | 01:01 |

Stimulation Parameters

| | |
|---|---|
| 01.0 ms | 05.0 V |

TABLE 8

Pulse Ratio, Trigger, Delay and Shape

| | |
|---|---|
| ^ | R Shape: Ramp |
|   | P Trig: Cont |
|   | P Delay: −15 ms |
| — | P Ratio: 01:01 |

The Pulse Ratio setting determines how often an electrical stimulus pulse is generated relative to the stretch protocols. The ratio is of the form:

pulse:stretch

A ratio of 1:1 indicates that every pacer Event will generate a stretch and a pulse. A value of 1:2 indicates that while stretches will occur on every Event, pulses will only be generated on every other Event. A ratio of 2:1 indicates the reverse: a pulse on every Event but a stretch on every other Event.

A ratio of 0:x results in stretches only while a ratio of x:0 results in pulses only.

The data in Tables 7 and 8 is used to generate the waveform of FIG. 1, wherein there is shown at the upper portion a stretch regiment applied to a cell culture; the regimen having five (5) parts: (a) a start phase of 10 ms with 15% stretch applied to the culture; (b) a contract phase of 10 ms wherein the stretch is reduced to 5% using a sine shape waveform; (c) a short phase where the contracted length is maintained at 5% stretch for a 5 ms dwell time; (d) a release phase where the cell culture is stretched to 15% over 25 ms using a linear waveform; and (e) an end phase for the remainder of the 75 ms event where the culture is maintained at 15% stretch. The stretch cycle is chronic and is repeated for as many cycles as desired. In the lower portion of FIG. 1, there is shown electrical stimulation applied to the cell culture concurrently during the same 75 ms interval as the applied stretch described above and shown in the upper part of FIG. 1. A pulse stimulation is pre-programmed to "trigger" 5 ms before the start of the "contract" phase and apply a bimodal +/−5 volt pulse to the cultured cells over a 5 ms interval between 5-10 ms of the 75 ms cell treatment illustrated. The electrical stimulation is repeated with the stretch for as many cycles as desired. In FIG. 1, Event represents the beginning of the synchronized electrical stimulation/stretch cycle, P Trig represents the pulse trigger for electrical stimulation and P Delay indicates a −5 ms trigger delay for electrical stimulation.

Generally speaking, there is thus provided in accordance with the invention an apparatus for providing synchronized chronic electrical stimulation and chronic stretch to a cell culture including: (a) a deformable cell culture container having a cavity for receiving cells or tissue; (b) at least two (2) electrodes disposed in the cavity of said deformable cell culture container; (c) means for providing chronic stretch to said deformable cell culture container; and (d) a programmable controller coupled to the two (2) electrodes and coupled to the means for providing chronic stretch to the deformable cell culture container, wherein the programmable controller has one or more electrical stimulation output(s) adapted to provide chronic electrical stimulation in the form of electrical stimulation pulses to the electrodes, the pulses being suitable for stimulating cells and the controller further having one or more stretch outputs coupled to the means for providing stretch to said container and thus provides a stretch control signal thereto, and wherein further the controller is adapted to synchronize the chronic electrical stimulation provided to the electrodes and the chronic stretch signals provided to the means for providing chronic stretch to the deformable cell culture container. The means for providing chronic stretch to said deformable cell culture container include the movable structures described in connection with the various figures as well as solenoids and the like attached to the culture container. In general, such means include any member attached or connected to the culture container which is movable with respect thereto and thus capable of providing stretch thereto.

In some embodiments, the apparatus includes a plurality of deformable cell culture containers having cavities for receiving cells or tissue, each cavity being provided with at least 2 electrodes disposed therein and each deformable container being coupled to means for providing chronic stretch to said cell culture containers and wherein the programmable controller has one or more electrical stimulation output(s) coupled to the electrodes disposed in each culture container adapted to provide chronic electrical stimulation in the form of electrical stimulation pulses suitable for stimulating cells and one or more stretch outputs coupled to the means for providing stretch to said containers and thus provides a stretch control signal thereto, and wherein further the controller is adapted to synchronize the chronic electrical stimulation provided to the electrodes and the chronic stretch signals provided to the means for providing chronic stretch to the deformable cell culture containers. The means for providing chronic stretch to the plurality of cell culture containers comprises a fixed support and a movable support upon both of which the plurality of cell culture containers are mounted in one preferred embodiment. So also, the electrodes are mounted on a removable printed circuit board attached to said fixed support. The fixed support optionally has a pair of contacts communicating with the controller corresponding to a pair of contacts provided on the circuit board and the circuit board is configured to selectively couple one of the electrodes of each cell culture container to one of the contacts of the circuit board.

In preferred cases, the apparatus is adapted to provide at least 15% stretch and pre-load to the culture cell container and the apparatus is configured and adapted to provide a stretch cycle frequency of up to 10 Hz.

The apparatus is typically configured and adapted to provide a stretch cycle which includes two (2) dynamic phases and three (3) static phases. The stretch cycle may have a static start phase with the same % stretch as a static end phase of the stretch cycle and the dynamic phases may include a contract phase wherein the culture cell container is contracted and a release phase wherein the culture cell container is lengthened. The contract phase and the release phase may be provided a temporal strain profile which is selected from linear profiles and sine wave profiles. In many cases, the cavity of the cell culture container is provided with an attachment factor for promoting cell adhesion thereto. The attachment factor may be selected from polylysine attachment factors, fibronectin attachment factors and collagen attachment factors.

In another aspect of the invention, there is provided an apparatus for providing synchronized chronic electrical stimulation and chronic stretch to a cell culture comprising: (a) a electromechanical stage having a movable portion coupled to a stepper motor for providing chronic motion to the movable portion of the electromechanical stage corresponding to rotation of the stepper motor; (b) a deformable cell culture container having a cavity for receiving cells or tissue mounted on the electromechanical stage and coupled to the movable portion thereof such that chronic stretch is applied to said deformable cell culture container corresponding to rotation of the stepper motor and the accompanying chronic motion of the movable portion of the electromechanical stage; (c) at least two (2) electrodes disposed in the cavity of said deformable cell culture container; and (d) a programmable controller coupled to the two (2) electrodes and the stepper motor, wherein the programmable controller has one or more electrical stimulation output(s) adapted to provide chronic electrical stimulation in the form of electrical stimulation pulses suitable for stimulating cells coupled to the electrodes and one or more stretch outputs coupled to the stepper motor and thus provides a control signal thereto for controlling its rotation, and wherein further the controller is adapted to synchronize the chronic electrical stimulation provided to the electrodes and the rotation imparted to the stepper motor to thereby provide synchronized chronic electrical stimulation and chronic stretch to cells or tissue disposed in the deformable cell culture container.

The apparatus may be provided with a plurality of deformable cell culture containers having cavities for receiving cells or tissue are mounted on the electromechanical stage and coupled to the movable portion thereof, and at least two (2) electrodes are disposed in the cavities of each container and coupled to the programmable controller and the movable portion of the electromechanical stage is adapted to move linearly with respect to a fixed portion of the electromechanical stage. The electrodes may be generally planar and mounted on a printed circuit board, and oriented in the direction of linear stretch applied to the cell culture containers. Optionally, the printed circuit board is provided with a plurality of viewing ports. and the movable portion of the electromechanical stage is mounted on a pair of guide rods.

A preferred construction is wherein the stepper motor drives a screw engaged to the movable portion of the electromechanical stage.

In yet another aspect of the present invention, there is provided a method of culturing cells including: (a) disposing cells in the cavity of a deformable cell culture container; and (b) applying synchronized chronic electrical stimulation and stretch to the cells in the deformable culture cell container. In this method, the synchronized chronic electrical stimulation may be applied in the form of pulses at a frequency of from 0.010-99 Hz and a duration of from 0.4 to 24 ms and the electrical stimulation may have a voltage from +/−1V to +/−40 V. Optionally, the synchronized electrical stimulation pulses are bipolar and the stretch cycles are applied to the cells at a frequency of from 0.010 to 15 Hz. The cells may be stretched at least 1% during a stretch cycle and stretched up to 50% during a stretch cycle, such as wherein the cells are stretched at least 5% during a stretch cycle; the cells are stretched at least 10% during a stretch cycle; the cells are stretched at least 20% during a stretch cycle; the cells are stretched at least 30% during a stretch cycle; the cells are stretched at least 40% during a stretch cycle.

The process may be controlled by a controller which generates a reference signal and wherein the chronic electrical stimulation is synchronized to the reference signal and chronic stretch cycles are synchronized to the reference signal, thereby synchronizing the chronic electrical stimulation to chronic stretch applied to the cells. Typically, the chronic electrical stimulation applied to the cells is concurrent with a stretch cycle applied to the cells and the culture cell container comprises silicone rubber. So also, the applied stretch comprises stretch cycles generally include two (2) dynamic phases and three (3) static phases and a stretch cycle has a static start phase with the same % stretch as a static end phase of the stretch cycle. In many preferred embodiments of the inventive process, the dynamic phases include a contract phase wherein the culture cell container is contracted and a release phase wherein the culture cell container is lengthened wherein the contract phase and the release phase have a temporal strain profile which is selected from linear profiles and sine wave profiles. In cases where additional conductivity is desirable, the process includes adding an electrolytic medium to the cell cavity of the deformable cell culture container. The electrolytic medium may be a culture medium which includes a salt and an amino acid. Cells processed in accordance with the invention include cells selected from: myocytes; stem cells; induced pluripotent stem cell derived cells; neurons; and neurolemmocytes or immortalized cell lines derived from cells with a cardiac, smooth or skeletal muscle origin.

In still yet another aspect of the invention, a method of culturing cells includes: (a) disposing cells in the cavity of a deformable cell culture container; and (b) adding an electrolytic medium to the cavity; (c) applying synchronized chronic electrical stimulation and stretch to the cells in the deformable culture cell container, wherein the synchronized chronic electrical stimulation is applied in the form of pulses at a frequency of from 0.010-99 Hz and a duration of from 0.4 to 24 ms and wherein stretch cycles are applied to the cells at a frequency of from 0.010 to 15 Hz.

While the invention has been described in detail, modifications within the spirit and scope of the invention will be readily apparent to those of skill in the art. Such modifications are also to be considered as part of the present invention. In view of the foregoing discussion, relevant knowledge in the art and references discussed above in connection with the Background of the Invention, the Summary of Invention and Detailed Description, the disclosures of which are all incorporated herein by reference, further description is deemed unnecessary. In addition, it should be understood from the foregoing discussion that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. An apparatus for providing synchronized chronic electrical stimulation and chronic stretch to a cell culture comprising:
   (a) a deformable cell culture container having a cavity for receiving cells or tissue;
   (b) at least two (2) electrodes disposed in the cavity of said deformable cell culture container;
   (c) means for providing chronic stretch to said deformable cell culture container; and
   (d) a programmable controller coupled to the two (2) electrodes and coupled to the means for providing chronic stretch to the deformable cell culture container, wherein the programmable controller has one or more electrical stimulation output(s) adapted to provide chronic electrical stimulation in the form of electrical stimulation pulses to the electrodes, the pulses being suitable for stimulating cells and the controller further having one or more stretch outputs coupled to the means for providing chronic stretch to said container and thus provides a chronic stretch control signal thereto,
   and wherein further the controller is adapted to synchronize the chronic electrical stimulation provided to the electrodes and the chronic stretch signals provided to the means for providing chronic stretch to the deformable cell culture container, such that there is a predetermined temporal relationship between recurring electrical stimulation and recurring stretch and wherein the controller and apparatus are adapted and configured such that the cells may be stretched at least 5% during a stretch cycle.

2. The apparatus according to claim 1, wherein the electrodes disposed in the cavity are carbon electrodes.

3. The apparatus according to claim 1, wherein the apparatus comprises a plurality of deformable cell culture containers having cavities for receiving cells or tissue, each cavity being provided with at least 2 electrodes disposed therein and each deformable container being coupled to means for providing chronic stretch to said cell culture containers and wherein the programmable controller has one or more electrical stimulation output(s) coupled to the electrodes disposed in each culture container adapted to provide chronic electrical stimulation in the form of electrical stimulation pulses suitable for stimulating cells and one or more stretch outputs coupled to the means for providing stretch to said containers and thus provides a stretch control signal thereto, and wherein further the controller is adapted to synchronize the chronic electrical stimulation provided to the electrodes and the chronic stretch signals provided to the means for providing chronic stretch to the deformable cell culture containers.

4. The apparatus according to claim 3, wherein the means for providing chronic stretch to the plurality of cell culture containers comprises a fixed support and a movable support upon both of which the plurality of cell culture containers are mounted.

5. The apparatus according to claim 4, wherein the electrodes disposed in the cavities are carbon electrodes.

6. The apparatus according to claim 4, wherein the electrodes of the cavities are mounted on a removable printed circuit board attached to said fixed support.

7. The apparatus according to claim 6, wherein the fixed support has a pair of contacts communicating with the controller corresponding to a pair of contacts provided on the circuit board and the circuit board is configured to selectively couple one of the electrodes of each cell culture container to one of the contacts of the circuit board.

8. The apparatus according to claim 1, controlled by a controller which generates a reference signal and wherein the chronic electrical stimulation is synchronized to the reference signal and chronic stretch cycles are synchronized to the reference signal, thereby synchronizing the chronic electrical stimulation to chronic stretch applied to the cells.

9. The apparatus according to claim 8, wherein the controller and apparatus are adapted and configured such that the chronic electrical stimulation applied to the cells is at least partially concurrent with a stretch cycle applied to the cells.

10. The apparatus according to claim 1, wherein the controller and apparatus are adapted and configured such that
the synchronized chronic electrical stimulation is applied in the form of pulses at a frequency of from 0.010-99 Hz and a duration of from 0.4 to 24 ms; and
stretch cycles are applied to the cells at a frequency of from 0.010 to 15 Hz.

11. The apparatus according to claim 10, wherein the controller and apparatus are adapted and configured such that the synchronized electrical stimulation pulses are bipolar.

12. The apparatus according to claim 10, wherein the controller and apparatus are adapted and configured to provide at least 15% stretch and pre-load to the culture cell container and the apparatus is configured and adapted to provide a stretch cycle frequency of up to 10 Hz.

13. The apparatus according to claim 10, wherein the controller and apparatus are adapted and configured such that the cells may be stretched at least 5% during a stretch cycle and stretched up to 50% during a stretch cycle.

14. The apparatus according to claim 13, wherein the controller and apparatus are adapted and configured such that the cells are stretched at least 10% during a stretch cycle.

15. The apparatus according to claim 13, wherein the controller and apparatus are adapted and configured such that the cells may be stretched at least 20% during a stretch cycle.

16. The apparatus according to claim 13, wherein the controller and apparatus are adapted and configured such that the cells are stretched at least 30% during a stretch cycle.

17. The apparatus according to claim 13, wherein the controller and apparatus are adapted and configured such that the cells may be stretched at least 40% during a stretch cycle.

18. An apparatus for providing synchronized chronic electrical stimulation and chronic stretch to a cell culture comprising:
(a) a electromechanical stage having a movable portion coupled to a stepper motor for providing chronic motion to the movable portion of the electromechanical stage corresponding to rotation of the stepper motor;
(b) a deformable cell culture container having a cavity for receiving cells or tissue mounted on the electromechanical stage and coupled to the movable portion thereof such that chronic stretch is applied to said deformable cell culture container corresponding to rotation of the stepper motor and the accompanying chronic motion of the movable portion of the electromechanical stage;
(c) at least two (2) electrodes disposed in the cavity of said deformable cell culture container; and
(d) a programmable controller coupled to the two (2) electrodes and the stepper motor,
wherein the programmable controller has one or more electrical stimulation output(s) adapted to provide chronic electrical stimulation in the form of electrical stimulation pulses suitable for stimulating cells coupled to the electrodes and one or more stretch outputs coupled to the stepper motor and thus provides a control signal thereto for controlling its rotation,
and wherein further the controller is adapted to synchronize the chronic electrical stimulation provided to the electrodes and the rotation imparted to the stepper motor to thereby provide synchronized chronic electrical stimulation and chronic stretch to cells or tissue disposed in the deformable cell culture container, such that there is a predetermined temporal relationship between recurring electrical stimulation and recurring stretch and wherein the controller and apparatus are adapted and configured such that the cells may be stretched at least 5% during a stretch cycle.

19. The apparatus according to claim 18, wherein the movable portion of the electromechanical stage is adapted to move linearly with respect to a fixed portion of the electromechanical stage.

20. The apparatus according to claim 19, wherein the movable portion of the electromechanical stage is mounted on a pair of guide rods.

21. The apparatus according to claim 20, wherein the stepper motor drives a screw engaged to the movable portion of the electromechanical stage.

* * * * *